(12) United States Patent
Yoshida et al.

(10) Patent No.: US 10,959,692 B2
(45) Date of Patent: Mar. 30, 2021

(54) X-RAY IMAGING APPARATUS

(71) Applicant: SHIMADZU CORPORATION, Kyoto (JP)

(72) Inventors: Koki Yoshida, Kyoto (JP); Keiichi Goto, Kyoto (JP); Dai Hirose, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 135 days.

(21) Appl. No.: 16/060,596

(22) PCT Filed: Dec. 9, 2015

(86) PCT No.: PCT/JP2015/084559
§ 371 (c)(1),
(2) Date: Jun. 8, 2018

(87) PCT Pub. No.: WO2017/098610
PCT Pub. Date: Jun. 15, 2017

(65) Prior Publication Data
US 2018/0368792 A1   Dec. 27, 2018

(51) Int. Cl.
A61B 6/00   (2006.01)
A61B 6/03   (2006.01)
A61B 6/04   (2006.01)

(52) U.S. Cl.
CPC .............. A61B 6/4452 (2013.01); A61B 6/00 (2013.01); A61B 6/03 (2013.01); A61B 6/04 (2013.01);
(Continued)

(58) Field of Classification Search
CPC ..... A61B 6/4441; A61B 6/027; A61B 6/4435; A61B 6/4452; A61B 6/547
See application file for complete search history.

(56) References Cited

U.S. PATENT DOCUMENTS 8,345,823 B2    1/2013  Zaiki
2007/0140427 A1*  6/2007  Jensen .................. A61B 6/481
                                                378/98.12
(Continued)

FOREIGN PATENT DOCUMENTS

JP    2010-162278    7/2010
JP    2010-201103    9/2010
(Continued)

OTHER PUBLICATIONS

English Translation of JP 2011-005343 (Year: 2011).*
(Continued)

Primary Examiner — Yara B Green
(74) Attorney, Agent, or Firm — Andrew F. Young, Esq.; Nolte Lackenbach Siegel

(57) ABSTRACT

An X-ray imaging apparatus includes an X-ray tube (1), an FPD (2), a holding unit (4) that holds the X-ray tube and the FPD, which face each other, a table (3) on which a subject is placed, and a control unit (5) that controls the movement of the holding unit so as to control an X-ray irradiation direction of the X-ray tube and an X-ray detection direction of the FPD in an interlocking response with a relative position of the table to the X-ray tube and the FPD or based on an operation during X-ray imaging, when the X-ray imaging apparatus performs the X-ray imaging while relatively moving the table with respect to the X-ray tube and the FPD.

12 Claims, 7 Drawing Sheets

(52) U.S. Cl.
CPC .......... *A61B 6/4208* (2013.01); *A61B 6/4441* (2013.01); *A61B 6/504* (2013.01); *A61B 6/542* (2013.01); *A61B 6/545* (2013.01); *A61B 6/464* (2013.01); *A61B 6/481* (2013.01)

(56) References Cited

U.S. PATENT DOCUMENTS

| | | | | |
|---|---|---|---|---|
| 2013/0028388 | A1* | 1/2013 | Yoshida | A61B 6/547 |
| | | | | 378/190 |
| 2015/0250442 | A1* | 9/2015 | Kojima | A61B 6/0457 |
| | | | | 378/62 |

FOREIGN PATENT DOCUMENTS

| | | |
|---|---|---|
| JP | 2011-005343 | 1/2011 |
| JP | 2014-144192 | 8/2014 |
| WO | WO 2011/125283 | 10/2011 |

OTHER PUBLICATIONS

JP 2017-554718, Notice of Reasons for Refusal dated Jun. 8, 2019, 4 pages—Japanese; 6 pages—English.
PCT/JP2015/084559, International Search Report and Written Opinion dated Feb. 23, 2016, 1 page—English, 5 pages—Japanese.
JP 2017-554718, Notice of Reasons for Refusal dated Oct. 29, 2019, 3 pages—Japanese; 3 pages—English.

\* cited by examiner

Start imaging

End imaging

*FIG. 4A*   *FIG. 4B*   *FIG. 4C*
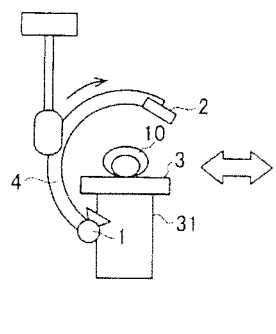
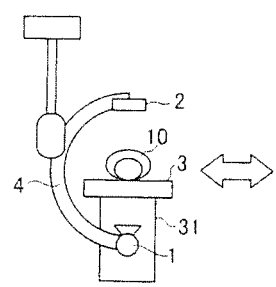
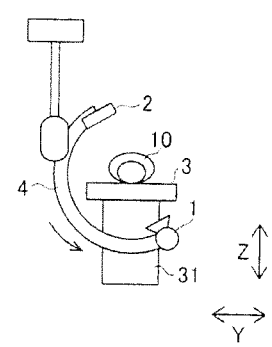

X-RAY IMAGING APPARATUS

CROSS REFERENCE TO RELATED APPLICATIONS

This application relates to, and claims priority from, PCT/JP2015/084559 filed Dec. 9, 2015, the entire contents of which are incorporated herein by reference.

FIGURE SELECTED FOR PUBLICATION

FIG. 1

BACKGROUND OF THE INVENTION

Field of the Invention

The present invention relates to an X-ray imaging apparatus, and more particularly, relates to an X-ray imaging apparatus that performs X-ray imaging while moving a table relative to an X-ray irradiation unit and an X-ray detection unit.

Description of the Related Art

Conventionally, an X-ray imaging apparatus that performs X-ray imaging while moving a table relative to an X-ray irradiation unit and an X-ray detection unit is known. Such an X-ray imaging apparatus is disclosed in Japanese Patent Laid-Open No. 2010-162278, for example.

An X-ray imaging apparatus disclosed in the aforementioned Japanese Patent Laid-Open No. 2010-162278 includes an X-ray tube that irradiates a subject with X-rays, an X-ray detector that detects the X-rays transmitted through the subject, a C-arm that holds the X-ray tube and the X-ray detector, which face each other, and can move the X-ray tube and the X-ray detector, and a table on which the subject is placed. This X-ray imaging apparatus performs X-ray imaging while moving the table relative to the X-ray tube and the X-ray detector. In addition, this X-ray imaging apparatus changes an X-ray imaging direction by rotating the C-arm.

Prior Art

Patent Document

Patent Document 1: Japanese Patent Laid-Open No. 2010-162278

ASPECTS AND SUMMARY OF THE INVENTION

Problem to be Solved by the Invention

However, in the X-ray imaging apparatus disclosed in the aforementioned Japanese Patent Laid-Open No. 2010-162278, when performing X-ray imaging while moving the table relative to the X-ray tube and the X-ray detector, an operator can change the X-ray imaging direction by rotating the C-arm, but the operator needs to operate the table and the C-arm separately. Therefore, there is a disadvantage that the operation burden on the operator increases. In addition, when the table and the C-arm are driven automatically, the table and the C-arm are operative independently, so that there are disadvantages that it is difficult to adjust the operation timing of the table and the C-arm, and it is difficult to image a specific part from a specific angular direction. Therefore, there is a problem that it is difficult to image the specific part from the specific angular direction while preventing an increase in the operation burden on the operator.

The present invention has been proposed in order to solve the aforementioned problem, and an object of the present invention is to provide an X-ray imaging apparatus that can image a specific part from a specific angular direction while preventing an increase in the operation burden on an operator.

Means for Solving the Problem

In order to attain the aforementioned object, an X-ray imaging apparatus according to an aspect of the present invention comprises an X-ray irradiation unit that irradiates a subject with X-rays, an X-ray detection unit that detects the X-rays transmitted through the subject, a holding unit that holds the X-ray irradiation unit and the X-ray detection unit, which face each other, and can move the X-ray irradiation unit and the X-ray detection unit, a table on which the subject is placed, and a control unit that controls the move of the holding unit so as to control an X-ray irradiation direction of the X-ray irradiation unit and an X-ray detection direction of the X-ray detection unit are respectively interlocked with a relative position of the table to the X-ray irradiation unit and the X-ray detection unit or the move of the holding unit so as to control the X-ray irradiation direction of the X-ray irradiation unit and the X-ray detection direction of the X-ray detection unit based on an operation during X-ray imaging when the X-ray imaging apparatus performs the X-ray imaging while moving the table relative to the X-ray irradiation unit and the X-ray detection unit.

As described above, when the X-ray imaging apparatus performs the X-ray imaging while moving the table relative to the X-ray irradiation unit and the X-ray detection unit, the control unit of the X-ray imaging apparatus according to the one aspect of the present invention controls the move of the holding unit to control the X-ray irradiation direction of the X-ray irradiation unit and the X-ray detection direction of the X-ray detection unit that are respectively interlocked with the relative position of the table to the X-ray irradiation unit and the X-ray detection unit or based on the operation during the X-ray imaging. Thus, when the X-ray irradiation direction of the X-ray irradiation unit and the X-ray detection direction of the X-ray detection unit (X-ray imaging direction) are controlled in the relative position of the table to the X-ray irradiation unit and the X-ray detection unit, the relative move of the table and the move of the X-ray imaging direction can be interlocked, so that the operator only needs to operate the move of the table. Consequently, an increase in the operation burden on the operator can be prevented. Furthermore, when the X-ray irradiation direction of the X-ray irradiation unit and the X-ray detection direction of the X-ray detection unit (X-ray imaging direction) are controlled based on the operation during the X-ray imaging, the operator only needs to manipulate the timing to change the X-ray imaging direction, so that the operator need not actually perform a separate operation for moving the X-ray irradiation unit and the X-ray detection unit. Consequently, an increase in the operation burden on the operator is prevented. In addition, in these cases, the timing between the relative move of the table and the move of the X-ray imaging direction can be easily adjusted, so that a specific part can be easily imaged from a specific angular direction. Consequently, the imaging of the specific part can be achieved from the specific angular direction while an increase in the operation burden on the operator is being prevented.

In the aforementioned X-ray imaging apparatus according to this aspect, the control unit preferably controls rotating the holding unit around a predetermined rotation axis interlocked with the relative position of the table to the X-ray irradiation unit and the X-ray detection unit, or controls rotating the holding unit around the predetermined rotation axis based on the operation during the X-ray imaging. According to such configuration, the X-ray imaging direction can be easily changed in accordance with the relative move of the table, so that an increase in the operation burden can be prevented. Furthermore, it is not necessary to increase the number of X-ray irradiation units and the number of X-ray detection units as compared with that imagings are performed from multiple directions at the same time, so that the apparatus configuration can be avoided to be complicated. In addition, an increase in the exposure dose can be prevented.

In this case, the control unit preferably controls the move of the holding unit so as to reciprocate-rotate the X-ray irradiation unit and the X-ray detection unit interlocked with the relative position of the table to the X-ray irradiation unit and the X-ray detection unit, or controls the move of the holding unit so as to reciprocate-rotate the X-ray irradiation unit and the X-ray detection unit based on the operation during the X-ray imaging. According to this configuration, the X-ray imaging direction can be swung at the desired relative position of the table, so that the imaging of the specific part from the specific angular direction can be more easily performed.

In the aforementioned configuration in which the control unit controls rotating the holding unit around the predetermined rotation axis, the control unit preferably controls the move of the holding unit such that the X-ray irradiation direction of the X-ray irradiation unit and the X-ray detection direction of the X-ray detection unit are the same as a preset direction interlocked with the relative position of the table to the X-ray irradiation unit and the X-ray detection unit, or to control the move of the holding unit such that the X-ray irradiation direction of the X-ray irradiation unit and the X-ray detection direction of the X-ray detection unit are the same as the preset direction based on the operation during the X-ray imaging. According to this configuration, the X-ray imaging direction is the same as a desired direction at the desired relative position of the table with high accuracy.

In the aforementioned X-ray imaging apparatus according to this aspect, the control unit preferably controls the X-ray irradiation direction of the X-ray irradiation unit and the X-ray detection direction of the X-ray detection unit by changing a rotation angle of the holding unit. According to this configuration, the X-ray imaging direction can be easily changed by changing the rotation angle of the holding unit.

In the aforementioned X-ray imaging apparatus according to this aspect, it is preferable that the X-ray irradiation direction of the X-ray irradiation unit and the X-ray detection direction of the X-ray detection unit are interlockingly controlled and the relative position of the table to the X-ray irradiation unit and the X-ray detection unit is pre-settable. According to this configuration, the X-ray imaging direction can be the desired direction at the desired relative position of the table with a higher accuracy.

In the aforementioned X-ray imaging apparatus according to this aspect, the control unit preferably controls the movement of the holding unit so as to control the X-ray irradiation direction of the X-ray irradiation unit and the X-ray detection direction of the X-ray detection unit based on a fact that the relative position of the table to the X-ray irradiation unit and the X-ray detection unit has reached a predetermined position. According to this configuration, the specific part can be easily imaged from the specific angular direction by changing the X-ray imaging direction according to the relative position of the table.

In the aforementioned X-ray imaging apparatus according to this aspect, it is preferable that the X-ray irradiation direction of the X-ray irradiation unit and the X-ray detection direction of the X-ray detection unit are presettable in association with the relative position of the table to the X-ray irradiation unit and the X-ray detection unit and the control unit controls the movement of the holding unit such that the X-ray irradiation direction of the X-ray irradiation unit and the X-ray detection direction of the X-ray detection unit coincide with a preset direction when the relative position of the table with respect to the X-ray irradiation unit and the X-ray detection unit reaches a predetermined intermediate position set in advance. According to this configuration, the X-ray imaging direction can be easily changed to the set-up direction interlocked with the relative position of the table, so that the specific part can be more easily imaged from the specific angular direction.

In this case, it is preferable that the X-ray irradiation direction of the X-ray irradiation unit and the X-ray detection direction of the X-ray detection unit are presettable in association with each of a first relative position and a second relative position of the table to the X-ray irradiation unit and the X-ray detection unit and the control unit controls such that the X-ray irradiation direction of the X-ray irradiation unit and the X-ray detection direction of the X-ray detection unit coincide with a preset first direction when the relative position of the table to the X-ray irradiation unit and the X-ray detection unit reaches the first relative position set in advance, and to perform control such that the X-ray irradiation direction of the X-ray irradiation unit and the X-ray detection direction of the X-ray detection unit coincide with a preset second direction when the relative position of the table to the X-ray irradiation unit and the X-ray detection unit reaches the second relative position. According to this configuration, X-ray imaging can be easily performed from a desired X-ray imaging direction at each of a plurality of relative positions of the table.

Effect of the Invention

As described above, according to the present invention, it is possible to image the specific part from the specific angular direction while an increase in the operation burden on the operator is being prevented.

The above and other aspects, features and advantages of the present invention will become apparent from the following description read in conjunction with the accompanying drawings, in which like reference numerals designate the same elements.

BRIEF DESCRIPTION OF THE DRAWINGS

FIGS. 4A, 4B, 4C are diagrams illustrating an operation of a movement of the X-ray imaging apparatus and a change of an imaging direction according to the embodiment of the present invention.

DETAILED DESCRIPTION OF THE PREFERRED EMBODIMENTS

Figure 1:
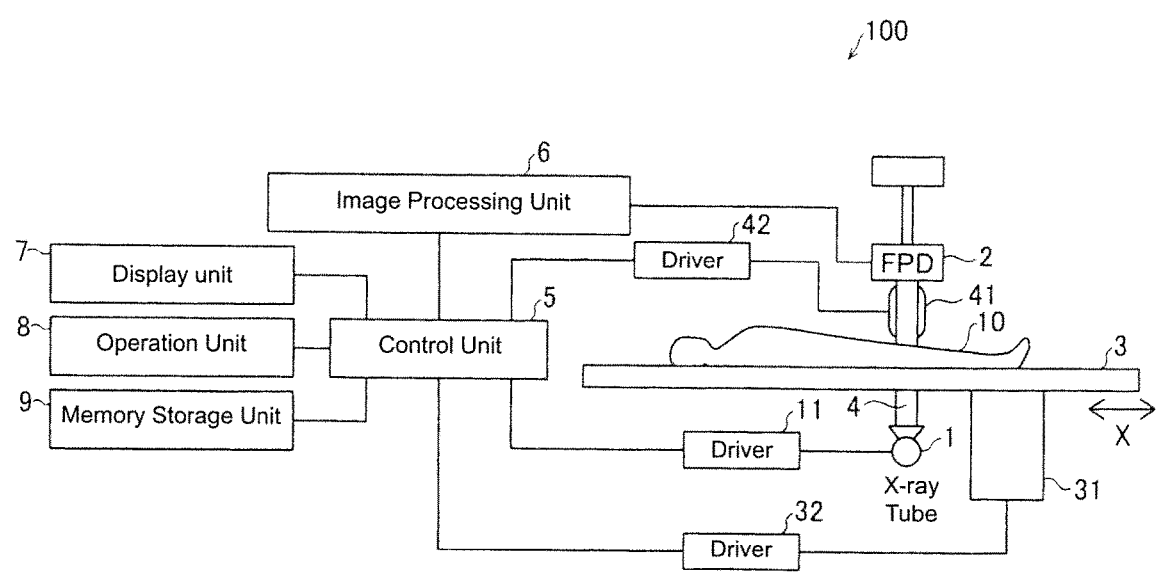
FIG. 1 is a schematic view showing the overall configuration of an X-ray imaging apparatus according to an embodiment of the present invention.

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

Modes for Carrying Out the Invention

An embodiment embodying the present invention is hereinafter described on the basis of the drawings.

Configuration of X-Ray Imaging Apparatus

First, the overall configuration of an X-ray imaging apparatus 100 according to the embodiment of the present invention is described with reference to all FIGS. 1 to 4C.

The X-ray imaging apparatus 100 according to the present embodiment performs an X-ray imaging while additionally relatively moving a subject 10 placed on a table 3. The X-ray imaging apparatus 100 includes an angiography apparatus that radiographs a blood vessel using a contrast medium, for example. As shown in FIG. 1, the X-ray imaging apparatus 100 comprises an X-ray tube 1, an FPD (flat panel detector) 2, the table 3, a holding unit 4, a control unit 5, an image processing unit 6, a display unit 7, an operation unit 8, and a memory storage unit 9. The X-ray tube 1 is connected to a driver 11. The table 3 moves in a horizontal direction (directions X and Y) by a table drive unit 31. The table drive unit 31 is connected to a driver 32. The holding unit 4 movably supports the X-ray tube 1 and the FPD 2. The holding unit 4 is driven by a drive unit 41 and rotates. The drive unit 41 is connected to a driver 42. The X-ray tube 1 is an example of the X-ray irradiation unit in the claims, and the FPD 2 is the example of an X-ray detection unit in the claims.

The X-ray imaging apparatus 100 radiographs the subject 10 (human body) lying on the table 3. Specifically, the X-ray imaging apparatus 100 detects, with the FPD 2, X-rays radiated from the X-ray tube 1 disposed below the table 3 and transmitted through the subject 10, and takes an X-ray image. Furthermore, the X-ray imaging apparatus 100 takes an X-ray image while moving the subject 10 (table 3) relative to the X-ray tube 1 and the FPD 2.

Figure 3A:
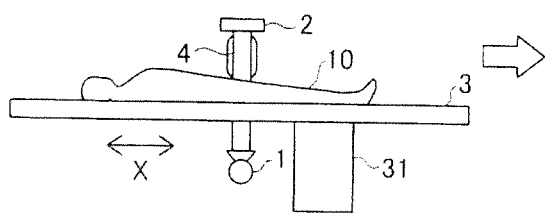
FIGS. 3A, 3B are diagrams illustrating an operation of a relative movement of a table of the X-ray imaging apparatus according to the embodiment of the present invention.
Figure 3B:
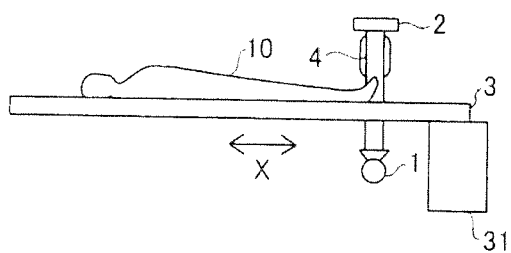

The X-ray imaging apparatus 100 is mainly used to image the lower limb blood vessel of the subject 10. Specifically, the contrast medium is injected into the blood vessel of the subject 10 in a state where the subject 10 is placed on the table 3. Then, X-ray imaging is performed while the table 3 is moving in the direction X so as to follow the flow of the contrast medium, as shown in FIG. 3A, FIG. 3B. That is, the range of X-ray imaging (the X-ray irradiation range of the X-ray tube 1 and the detection range of the FPD 2) does not include the entire lower limb of the subject 10, so that X-ray imaging is performed while the subject 10 (table 3) is moving relative to the X-ray tube 1 and the FPD 2. For example, X-ray imaging is started from the base of the lower limb of the subject 10, and the X-ray imaging is terminated when the tip (toe) of the lower limb of the subject 10 is reached.

Figure 2:
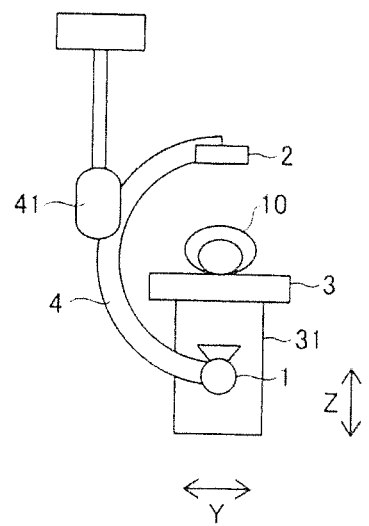
FIG. 2 is a side view showing the X-ray imaging apparatus according to the embodiment of the present invention.

As shown in FIGS. 1 and 2, the X-ray tube 1 faces the FPD 2 sandwiching the table 3. The X-ray tube 1 irradiates the subject 10 lying on the table 3 with X-rays. The X-ray tube 1 is driven by the driver 11 to generate X-rays. The driver 11 is connected to the control unit 5. Furthermore, the X-ray tube 1 can adjust the intensity and irradiation range of X-rays to be generated.

The FPD 2 detects the X-rays radiated from the X-ray tube 1 and transmitted through the subject 10. The FPD 2 images an X-ray image based on the detected X-rays. Specifically, the FPD 2 converts the detected X-rays to an electrical signal. Information about the X-rays converted to the electric signal is transmitted to the image processing unit 6.

The X-ray tube 1 and the FPD 2 start imaging an X-ray image based on an instruction to start imaging input via the operation unit 8 from a user (practitioner). That is, based on the user's instruction to start imaging, the X-ray tube 1 radiates X-rays, and the FPD 2 detects the X-rays. In addition, the X-ray tube 1 and the FPD 2 terminates or suspends imaging an X-ray image based on an instruction to terminate imaging or suspend imaging, input via the operation unit 8 from the user. That is, based on the user's instruction to terminate imaging or suspend imaging, the X-ray tube 1 stops radiating the X-rays, and the FPD 2 stops detecting the X-rays.

As shown in FIGS. 3A, 3B, the table 3 is movable relative to the X-ray tube 1 and the FPD 2 in a state where the subject 10 lies (is placed) thereon. Specifically, the table 3 is movable in the body axis direction (direction X) of the lying subject 10 and a direction (direction Y) perpendicular to the body axis direction of the subject 10. The table 3 moves in the horizontal direction by the table drive unit 31 disposed at the lower side. In other words, the table 3 moves by the table drive unit 31 based on the operation of the user or a set-up route. The table drive unit 31 is connected to the control unit 5 via the driver 32. The control unit 5 controls the table drive unit 31 to drive the table 3. When the table 3 is driven by the table drive unit 31, the route and speed are controlled with a pre-registered program. In addition, when the table 3 is driven by the table drive unit 31, the table 3 can be driven based on the operation of the user. Furthermore, the table 3 can be moved in the horizontal direction manually by the user.

The holding unit 4 holds the X-ray tube 1 and the FPD 2 such that the X-ray tube 1 and the FPD 2 face each other. The holding unit 4 has a C-shape curved to bypass the table 3. The X-ray tube 1 is disposed in the vicinity of a lower end of the holding unit 4, and the FPD 2 is disposed in the vicinity of an upper end of the holding unit 4. As shown in FIG. 4A-FIG. 4C, the holding unit 4 moves the X-ray tube 1 and the FPD 2. Specifically, the holding unit 4 moves such that the X-ray tube 1 and the FPD 2 face each other at a predetermined angle with respect to a vertical direction (direction Z) referencing a position where the X-ray tube 1 and the FPD 2 face each other in the vertical direction.

The holding unit 4 rotates around a predetermined rotation axis. When the holding unit 4 rotates around the body axis direction (direction X) of the subject 10, for example, the holding unit 4 performs a pendulum motion (swinging). When the holding unit 4 rotates around the vertical direction (direction Z), the holding unit 4 performs a precession motion. The holding unit 4 is driven by the drive unit 41.

The drive unit 41 is attached to a ceiling and supports the holding unit 4 from above. That is, the X-ray imaging apparatus 100 is a ceiling-suspended X-ray imaging apparatus. The drive unit 41 is connected to the control unit 5 via the driver 42. The control unit 5 controls the drive unit 41 to drive the holding unit 4.

The control unit 5 controls each unit of the X-ray imaging apparatus 100. Specifically, the control unit 5 controls the X-ray tube 1 via the driver 11. Furthermore, the control unit 5 controls driving of the table drive unit 31 via the driver 32. The control unit 5 also controls driving of the drive unit 41 via the driver 42. In addition, the control unit 5 controls the display unit 7 to display an X-ray image generated by the image processing unit 6. The control unit 5 receives an operation via the operation unit 8. The control unit 5 controls the memory storage unit 9 to store the X-ray image.

The image processing unit 6 generates an X-ray image based on the X-rays detected by the FPD 2. The display unit 7 displays a captured X-ray image. The display unit 7 also displays information about the state of the X-ray imaging apparatus 100, an image relating to the operation of the X-ray imaging apparatus 100, etc.

The operation unit 8 receives an operation input from the user. The operation unit 8 comprises a mouse, a keyboard, a touch panel, a foot switch, a hand switch, or the like, for example. The X-ray imaging apparatus 100 is operated by operating the operation unit 8.

According to the present embodiment, the control unit 5 controls movement of the holding unit 4 so as to control the X-ray irradiation direction of the X-ray tube 1 and the X-ray detection direction of the FPD 2 (X-ray imaging direction) interlocked with the relative position of the table 3 with respect to the X-ray tube 1 and the FPD 2 when the X-ray imaging apparatus 100 performs X-ray imaging while moving the table 3 relative to the X-ray tube 1 and the FPD 2. The relative position of the table 3 to the X-ray tube 1 and the FPD 2 interlocked with which the X-ray irradiation direction of the X-ray tube 1 and the X-ray detection direction of the FPD 2 are controlled is presettable. In addition, the control unit 5 controls the movement of the holding unit 4 so as to control the X-ray irradiation direction of the X-ray tube 1 and the X-ray detection direction of the FPD 2 based on the operation of the user during X-ray imaging.

Specifically, the control unit 5 controls rotating the holding unit 4 around the predetermined rotation axis interlocked with the relative position of the table 3 to the X-ray tube 1 and the FPD 2. In addition, the control unit 5 controls rotating the holding unit 4 around the predetermined rotation axis based on the operation during X-ray imaging. The control unit 5 controls the movement of the holding unit 4 so as to reciprocate-rotate the X-ray tube 1 and the FPD 2 interlocked with the relative position of the table 3 with respect to the X-ray tube 1 and the FPD 2. Furthermore, the control unit 5 controls the movement of the holding unit 4 so as to reciprocate-rotate the X-ray tube 1 and the FPD 2 based on the operation during X-ray imaging.

In addition, the control unit 5 controls the movement of the holding unit 4 such that the X-ray irradiation direction of the X-ray tube 1 and the X-ray detection direction of the FPD 2 (X-ray imaging direction) coincide with a preset direction in interlocking with the relative position of the table 3 to the X-ray tube 1 and the FPD 2. In addition, the control unit 5 controls the movement of the holding unit 4 such that the X-ray irradiation direction of the X-ray tube 1 and the X-ray detection direction of the FPD 2 coincide with the preset direction based on the operation during X-ray imaging. The control unit 5 controls the X-ray irradiation direction of the X-ray tube 1 and the X-ray detection direction of the FPD 2 by changing the rotation angle of the holding unit 4.

In addition, the control unit 5 controls the movement of the holding unit 4 so as to control the X-ray irradiation direction of the X-ray tube 1 and the X-ray detection direction of the FPD 2 when the relative position of the table 3 with respect to the X-ray tube 1 and the FPD 2 reaches a predetermined position.

According to the present embodiment, the X-ray irradiation direction of the X-ray tube 1 and the X-ray detection direction of the FPD 2 (X-ray imaging direction) are presettable in association with the relative position of the table 3 to the X-ray tube 1 and the FPD 2. The control unit 5 controls movement of the holding unit 4 such that the X-ray irradiation direction of the X-ray tube 1 and the X-ray detection direction of the FPD 2 coincide with the preset direction when the relative position of the table 3 to the X-ray tube 1 and the FPD 2 reaches a predetermined intermediate position set in advance.

For example, the X-ray irradiation direction of the X-ray tube 1 and the X-ray detection direction of the FPD 2 are presettable in association with each of a first relative position and a second relative position of the table 3 to the X-ray tube 1 and the FPD 2. The control unit 5 is configured to perform control such that the X-ray irradiation direction of the X-ray tube 1 and the X-ray detection direction of the FPD 2 coincide with a preset first direction when the relative position of the table 3 to the X-ray tube 1 and the FPD 2 reaches the first relative position set in advance, and to perform control such that the X-ray irradiation direction of the X-ray tube 1 and the X-ray detection direction of the FPD 2 coincide with a preset second direction when the relative position of the table 3 to the X-ray tube 1 and the FPD 2 reaches the second relative position.

First Operation Example

Figure 5:
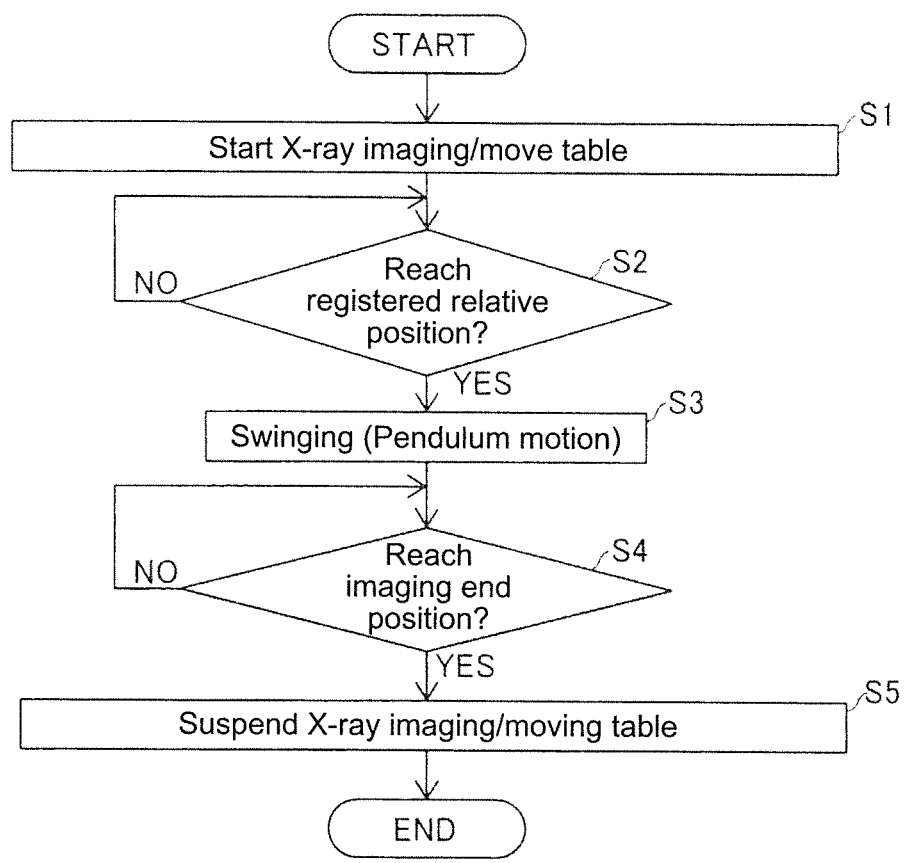
FIG. 5 is a flowchart (decision tree) illustrating X-ray imaging procedure (protocol) of a first operation example performed by the X-ray imaging apparatus according to the embodiment of the present invention.

Next, X-ray imaging processing of a first operation example performed by the X-ray imaging apparatus 100 according to the present embodiment is described with reference to FIG. 5. In the first operation example, an example in which a change in the X-ray imaging direction is started interlockingly with the relative movement of the table 3 to the X-ray tube 1 and the FPD 2 is described.

Once the X-ray imaging apparatus 100 receives an instruction to start imaging via the operation unit 8 from the user in a state where the relative position of the table 3, at which a pendulum motion of the X-ray tube 1 and the FPD 2 is started, is registered, while the subject (a person to be imaged) 10 is lying (is placed) on the table 3, the X-ray imaging apparatus 100 starts X-ray imaging in the step S1. At this time, the movement of the table 3 is started. Specifically, X-rays are radiated from the X-ray tube 1. The X-rays are detected by the FPD 2, and an X-ray image is generated by the image processing unit 6. Furthermore, the table 3 is moved relative to the X-ray tube 1 and the FPD 2. In addition, the table 3 can be automatically moved along a registered trajectory or can be manually moved by the user.

In the step S2, it is determined whether or not the table 3 has reached the registered relative position. That is, it is determined whether or not the table 3 has reached the registered relative position as the table 3 is moved relative to the X-ray tube 1 and the FPD 2 during X-ray imaging. When the table 3 has not reached the registered relative position, the determination in the step S2 is repeated, and when the table 3 has reached the registered relative position, the processing advances to the step S3.

In the step S3, the pendulum motion of the X-ray tube 1 and the FPD 2 is started. Specifically, the holding unit 4 is driven, and the X-ray tube 1 and the FPD 2 are rotated around the body axis direction (direction X) of the subject 10 as a rotation axis. In the step S4, it is determined whether or not the table 3 has reached an imaging end position. When the table 3 has not reached the imaging end position, the determination in the step S4 is repeated, and when the table 3 has reached the imaging end position, the processing advances to the step S5.

In the step S5, X-ray imaging is stopped. At this time, the movement of the table 3 is stopped. Specifically, the radiation of X-rays from the X-ray tube 1 is stopped. When the table 3 moves automatically, the movement of the table 3 is stopped. Thereafter, the X-ray imaging processing is terminated.

Second Operation Example

Figure 6:
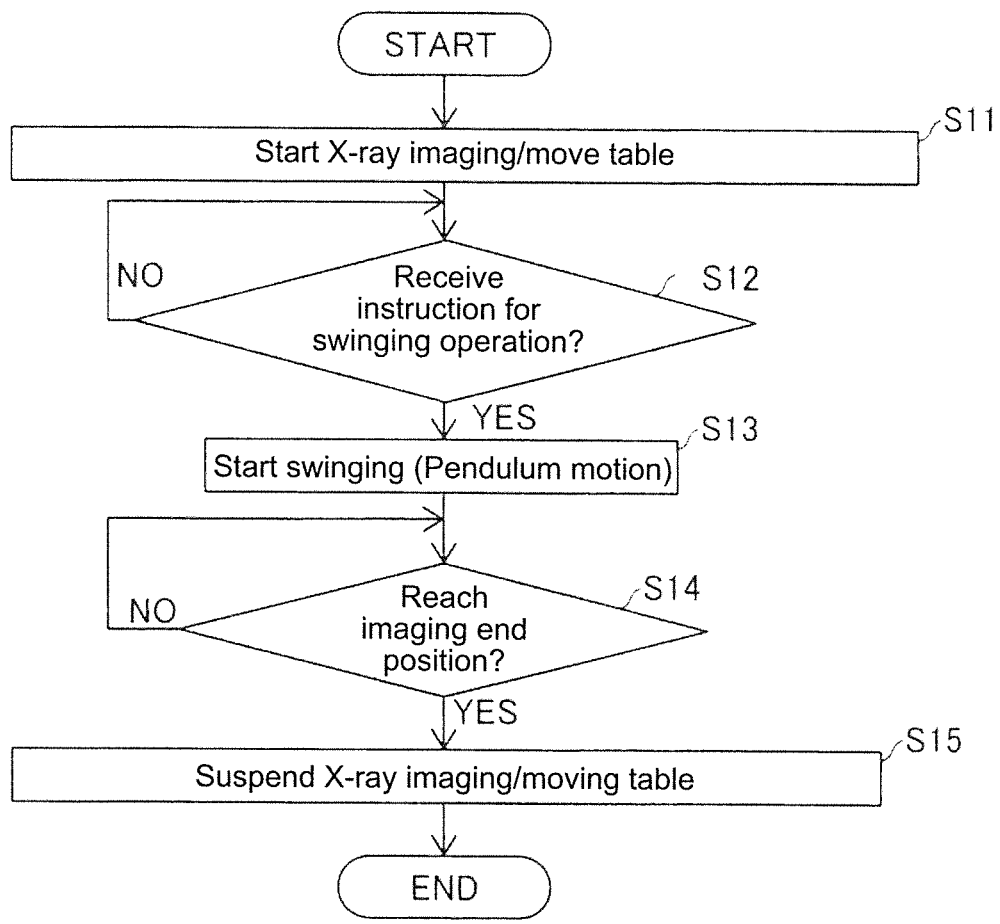
FIG. 6 is a flowchart illustrating X-ray imaging procedure (protocol) of a second operation example performed by the X-ray imaging apparatus according to the embodiment of the present invention.

Next, X-ray imaging processing of a second operation example performed by the X-ray imaging apparatus 100 according to the present embodiment is described with reference to FIG. 6. In the second operation example, an example in which a change in the X-ray imaging direction is started based on the operation of the user during X-ray imaging is described.

When the subject (a person to be imaged) 10 lies (is placed) on the table 3, and the X-ray imaging apparatus 100 receives an instruction to start imaging via the operation unit 8 from the user, the X-ray imaging apparatus 100 starts X-ray imaging in the step S11. At this time, the movement of the table 3 is started. Specifically, X-rays are radiated from the X-ray tube 1. The X-rays are detected by the FPD 2, and an X-ray image is generated by the image processing unit 6. Furthermore, the table 3 is moved relative to the X-ray tube 1 and the FPD 2. In addition, the table 3 can be automatically moved along the registered trajectory or can be manually moved by the user.

In the step S12, it is determined whether or not an operation for starting a pendulum motion has been received. Specifically, it is determined whether or not an operation for starting a pendulum motion to change the X-ray imaging direction has been received via the operation unit 8 from the user. When the operation has not been received, the determination in the step S12 is repeated, and when the operation has been received, the processing advances to the step S13.

In the step S13, the pendulum motion of the X-ray tube 1 and the FPD 2 is started. Specifically, the holding unit 4 is driven, and the X-ray tube 1 and the FPD 2 are rotated around the body axis direction (direction X) of the subject 10 as a rotation axis. In the step S14, it is determined whether or not the table 3 has reached the imaging end position. When the table 3 has not reached the imaging end position, the decision test in the step S14 is repeated, and when the table 3 has reached the imaging end position, the processing advances to the step S15.

In the step S15, the X-ray imaging is suspended. At this time, the movement of the table 3 is suspended. Specifically, the radiation of X-rays from the X-ray tube 1 is suspended. When the table 3 moves automatically, the movement of the table 3 is suspended. Thereafter, the X-ray imaging processing is terminated.

Third Operation Example

Figure 7:
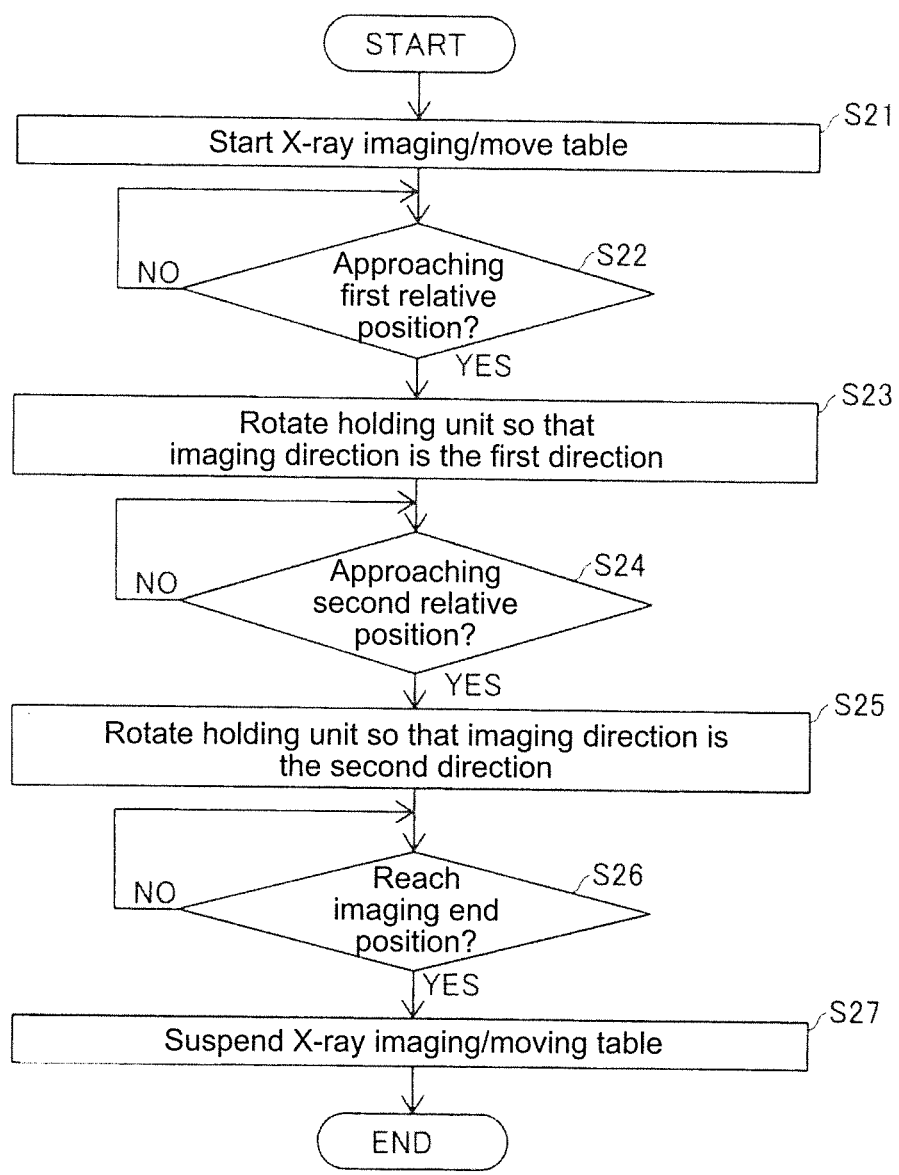
FIG. 7 is a flowchart illustrating X-ray imaging procedure (protocol) of a third operation example performed by the X-ray imaging apparatus according to the embodiment of the present invention.

Next, X-ray imaging processing of a third operation example performed by the X-ray imaging apparatus 100 according to the present embodiment is described with reference to FIG. 7. In the third operation example, an example in which the X-ray imaging direction is changed to a predetermined direction in association with the relative position of the table 3 to the X-ray tube 1 and the FPD 2 is described.

When the subject 10 (a person to be imaged) lies (is placed) on the table 3, and the X-ray imaging apparatus 100 receives an instruction to start imaging via the operation unit 8 from the user in a state where the relative position of the table 3 at which a pendulum motion of the X-ray tube 1 and the FPD 2 is started has been registered, the X-ray imaging apparatus 100 starts the X-ray imaging in the step S21. At this time, the movement of the table 3 is started. Specifically, X-rays are radiated from the X-ray tube 1. The X-rays are detected by the FPD 2, and an X-ray image is generated by the image processing unit 6. Furthermore, the table 3 is moved relative to the X-ray tube 1 and the FPD 2. In addition, the table 3 can be automatically moved along the registered trajectory or can be manually moved by the user.

In the step S22, it is determined whether or not the table 3 has approached the registered first relative position. That is, it is determined whether or not the table 3 has approached the registered first relative position as the table 3 is moved relative to the X-ray tube 1 and the FPD 2 during X-ray imaging. When the table 3 has not approached the registered first relative position, the determination in the step S22 is repeated, and when the table 3 has approached the registered first relative position, the processing advances to the step S23.

In the step S23, the holding unit 4 is rotated such that the X-ray imaging direction coincides with the first direction. Specifically, before the table 3 reaches the first relative position, the holding portion 4 is rotationally driven such that the X-ray imaging direction coincides with the first direction.

In the step S24, it is determined whether or not the table 3 has approached the registered second relative position.

That is, it is determined whether or not the table 3 has approached the registered second relative position as the table 3 is further moved relative to the X-ray tube 1 and the FPD 2 during X-ray imaging. When the table 3 has not approached the registered second relative position, the determination in the step S24 is repeated, and when the table 3 has approached the registered second relative position, the processing advances to the step S25.

In the step S25, the holding unit 4 is rotated such that the X-ray imaging direction coincides with the second direction. Specifically, before the table 3 reaches the second relative position, the holding unit 4 is rotationally driven such that the X-ray imaging direction coincides with the second direction. If the relative position of the table 3 and the X-ray imaging direction are further associated with each other, and another relative position in addition to the first relative position and the second relative position is registered, processing similar to that in the step S23 to the step S25 is repeated the number of times corresponding to the number of registered relative positions.

In the step S26, it is determined whether or not the table 3 has reached the imaging end position. When the table 3 has not reached the imaging end position, the determination in the step S26 is repeated, and when the table 3 has reached the imaging end position, the processing advances to the step S27.

In the step S27, the X-ray imaging is stopped. At this time, the movement of the table 3 is suspended. Specifically, the radiation of X-rays from the X-ray tube 1 is suspended. When the table 3 moves automatically, the movement of the table 3 is suspended. Thereafter, the X-ray imaging processing is terminated.

According to the present embodiment, as described above, the X-ray imaging apparatus 100 comprises the control unit 5 that controls the movement of the holding unit 4 so as to control the X-ray irradiation direction of the X-ray tube 1 and the X-ray detection direction of the FPD 2 interlocked with the relative position of the table 3 to the X-ray tube 1 and the FPD 2 or based on the operation during X-ray imaging when the X-ray imaging apparatus 100 performs the X-ray imaging while moving the table 3 relative to the X-ray tube 1 and the FPD 2. Thus, when the X-ray irradiation direction of the X-ray tube 1 and the X-ray detection direction of the FPD 2 (X-ray imaging direction) are controlled in interlocking with the relative position of the table 3 to the X-ray tube 1 and the FPD 2, relative movement of the table 3 and the movement of the X-ray imaging direction can be interlocked, so that an operator only needs to operate the movement of the table 3. Consequently, it is possible to significantly reduce or prevent an increase in the operation burden on the operator. Furthermore, when the X-ray irradiation direction of the X-ray tube 1 and the X-ray detection direction of the FPD 2 (X-ray imaging direction) are controlled based on the operation during X-ray imaging, the operator only needs to manipulate the timing to change the X-ray imaging direction, so that it is not necessary to perform an actual operation for moving the X-ray tube 1 and the FPD 2. Consequently, it is possible to significantly reduce or prevent an increase in the operation burden on the operator. In addition, in these cases, the timing between the relative movement of the table 3 and the movement of the X-ray imaging direction can be easily adjusted with each other, so that a specific part can be easily imaged from a specific angular direction. Consequently, it is possible to image the specific part from the specific angular direction while an increase in the operation burden on the operator is being prevented.

According to the present embodiment, as described above, the control unit 5 controls of rotating the holding unit 4 around the predetermined rotation axis interlocking with the relative position of the table 3 to the X-ray tube 1 and the FPD 2 or based on the operation during X-ray imaging. Thus, the X-ray imaging direction can be easily changed in accordance with the relative movement of the table 3, so that an increase in the operation burden can be effectively prevented. Furthermore, it is not necessary to increase the number of X-ray tubes 1 and the number of FPDs 2 as compared with the case where imaging is performed from multiple directions at the same time, so that the apparatus configuration can be avoided to be complicated. In addition, an increase in the exposure dose can be prevented.

According to the present embodiment, as described above, the control unit 5 controls the movement of the holding unit 4 so as to reciprocate-rotate the X-ray tube 1 and the FPD 2 in interlocking with the relative position of the table 3 to the X-ray tube 1 and the FPD 2 or based on the operation during X-ray imaging. Thus, the X-ray imaging direction can be swung at the desired relative position of the table 3, so that the specific part from the specific angular direction can be more easily imaged.

According to the present embodiment, as described above, the control unit 5 controls the movement of the holding unit 4 such that the X-ray irradiation direction of the X-ray tube 1 and the X-ray detection direction of the FPD 2 coincide with the preset direction in interlocking with the relative position of the table 3 to the X-ray tube 1 and the FPD 2 or based on the operation during X-ray imaging. Thus, the X-ray imaging direction can coincide with a desired direction at the desired relative position of the table 3 with high accuracy.

According to the present embodiment, as described above, the control unit 5 controls the X-ray irradiation direction of the X-ray tube 1 and the X-ray detection direction of the FPD 2 by changing the rotation angle of the holding unit 4. Thus, the X-ray imaging direction can be easily changed by changing the rotation angle of the holding unit 4.

According to the present embodiment, as described above, the relative position of the table 3 to the X-ray tube 1 and the FPD 2 interlocked with which the X-ray irradiation direction of the X-ray tube 1 and the X-ray detection direction of the FPD 2 are controlled is presettable. Thus, the X-ray imaging direction can coincide with the desired direction at the desired relative position of the table 3 with higher accuracy.

According to the present embodiment, as described above, the control unit 5 controls the movement of the holding unit 4 so as to control the X-ray irradiation direction of the X-ray tube 1 and the X-ray detection direction of the FPD 2 based on the fact that the relative position of the table 3 to the X-ray tube 1 and the FPD 2 has reached the predetermined position. Thus, the specific part can be easily imaged from the specific angular direction by changing the X-ray imaging direction according to the relative position of the table 3.

According to the present embodiment, as described above, the X-ray irradiation direction of the X-ray tube 1 and the X-ray detection direction of the FPD 2 are presettable in association with the relative position of the table 3 to the X-ray tube 1 and the FPD 2. Furthermore, the control unit 5 controls the movement of the holding unit 4 such that the X-ray irradiation direction of the X-ray tube 1 and the X-ray detection direction of the FPD 2 coincide with the preset direction when the relative position of the table 3 to the X-ray tube 1 and the FPD 2 reaches the predetermined intermediate position set in advance. Thus, the X-ray imaging direction can be easily changed to the set-up direction in interlocking with the relative position of the table 3, so that the specific part can be more easily imaged from the specific angular direction.

According to the present embodiment, as described above, the X-ray irradiation direction of the X-ray tube 1 and the X-ray detection direction of the FPD 2 are presettable in association with each of the first relative position and the second relative position of the table 3 to the X-ray tube 1 and the FPD 2. Furthermore, the control unit 5 controls such that the X-ray irradiation direction of the X-ray tube 1 and the X-ray detection direction of the FPD 2 coincide with the preset first direction when the relative position of the table 3 to the X-ray tube 1 and the FPD 2 reaches the first relative position set in advance, and the control unit 5 controls such that the X-ray irradiation direction of the X-ray tube 1 and the X-ray detection direction of the FPD 2 coincide with the preset second direction when the relative position of the table 3 to the X-ray tube 1 and the FPD 2 reaches the second relative position. Thus, X-ray imaging can be easily performed from a desired X-ray imaging direction at each of a plurality of relative positions of the table 3.

Modified Examples

The embodiment disclosed this time must be considered as illustrative in all points and not restrictive. The range of the present invention is not shown by the above description of the embodiment but by the scope of claims for patent, and all modifications (modified example) within the meaning and range equivalent to the scope of claims for patent are further included.

For example, while the example in which the subject is a human has been shown in the aforementioned embodiment, the present invention is not restricted to this. According to the present invention, the subject may be an organism other than a human or may be a thing. For example, the X-ray imaging apparatus according to the present invention may be used for medical equipment such as an X-ray apparatus or may be used for industrial equipment such as an X-ray inspection apparatus (non-destructive inspection apparatus). Alternatively, the X-ray imaging apparatus according to the present invention may be used for analytical equipment or the like.

While the example in which the lying subject is imaged has been shown in the aforementioned embodiment, the present invention is not restricted thereto. According to the present invention, a standing subject (in the standing position) may be imaged.

While the example, in which the X-ray imaging apparatus according to the present invention performs X-ray imaging, has been shown in the aforementioned embodiment, the present invention is not restricted thereto. The X-ray imaging apparatus according to the present invention may perform X-ray fluoroscopy for fluoroscopic examination or the like.

While the example in which the table is moved such that the table is moved relative to the X-ray tube (X-ray irradiation unit) and the FPD (X-ray detection unit) has been shown in the aforementioned embodiment, the present invention is not restricted thereto. According to the present invention, the X-ray irradiation unit and the X-ray detection unit may be moved such that the table is moved relative to the X-ray irradiation unit and the X-ray detection unit. Alternatively, all of the X-ray irradiation unit, the X-ray detection unit, and the table may be moved such that the table is moved relative to the X-ray irradiation unit and the X-ray detection unit.

While the example in which the X-ray irradiation direction of the X-ray tube and the X-ray detection direction of the FPD (X-ray imaging direction) are preset in association with the two relative positions of the table with respect to the X-ray tube (X-ray irradiation unit) and the FPD (X-ray detection unit) has been shown in the aforementioned embodiment, the present invention is not restricted thereto. According to the present invention, the X-ray irradiation direction of the X-ray irradiation unit and the X-ray detection direction of the X-ray detection unit (X-ray imaging direction) may be preset in association with one, or three or more relative positions of the table to the X-ray irradiation unit and the X-ray detection unit.

While the example in which the ceiling-suspended X-ray imaging apparatus including the holding unit suspended from the ceiling is used has been shown in the aforementioned embodiment, the present invention is not restricted thereto. For example, the present invention may be applied to a floor-standing X-ray imaging apparatus including a holding unit supported on the floor.

While the example in which the C-arm type X-ray imaging apparatus including the X-ray tube (X-ray irradiation unit) and the FPD (X-ray detection unit) supported by a support is used has been shown in the aforementioned embodiment, the present invention is not restricted thereto. For example, the present invention can be applied to an island type X-ray imaging apparatus.

While the processing of the X-ray imaging apparatus according to the present invention has been illustrated using a flowchart (decision tree) in a flow-driven manner in which processing is performed in turn along a processing flow for the convenience of illustration in the aforementioned embodiment, the present invention is not restricted thereto. According to the present invention, processing operations may be performed in an event-driven manner in which processing is performed on an event basis. In this case, the processing operations may be performed in a complete event-driven manner or in a combination of an event-driven manner and a flow-driven manner.

DESCRIPTION OF REFERENCE SIGNS

1 X-ray tube (X-ray irradiation unit)
2 FPD (X-ray imaging unit)
3 Table
4 holding unit
5 Control unit
10 Subject
100 X-ray imaging apparatus It will be further understood by those of skill in the art that the apparatus and devices and the elements herein, without limitation, and including the sub components such as operational structures, circuits, communication pathways, and related elements, control elements of all kinds, display circuits and display systems and elements, any necessary driving elements, inputs, sensors, detectors, memory elements, processors and any combinations of these structures etc. as will be understood by those of skill in the art as also being identified as or capable of operating the systems and devices and subcomponents noted herein and structures that accomplish the functions without restrictive language or label requirements since those of skill in the art are well versed in related X-Ray imaging apparatus and devices, computer and operational controls and technologies of radiographic devices and all their sub components, including various circuits and combinations of circuits without departing from the scope and spirit of the present invention.

Although only a few embodiments have been disclosed in detail above, other embodiments are possible and the inventors intend these to be encompassed within this specification. The specification describes certain technological solutions to solve the technical problems that are described expressly and inherently in this application. This disclosure describes embodiments, and the claims are intended to cover any modification or alternative or generalization of these embodiments which might be predictable to a person having ordinary skill in the art.

Those of skill would further appreciate that the various illustrative logical blocks, modules, circuits, and algorithm steps described in connection with the embodiments disclosed herein may be implemented as electronic hardware, computer software running on a specific purpose machine that is programmed to carry out the operations described in this application, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the exemplary embodiments.

The various illustrative logical blocks, modules, and circuits described in connection with the embodiments disclosed herein, may be implemented or performed with a general or specific purpose processor, or with hardware that carries out these functions, e.g., a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. The processor can be part of a computer system that also has an internal bus connecting to cards or other hardware, running based on a system BIOS or equivalent that contains startup and boot software, system memory which provides temporary storage for an operating system, drivers for the hardware and for application programs, disk interface which provides an interface between internal storage device(s) and the other hardware, an external peripheral controller which interfaces to external devices such as a backup storage device, and a network that connects to a hard wired network cable such as Ethernet or may be a wireless connection such as a RF link running under a wireless protocol such as 802.11. Likewise, an external bus may be any of but not limited to hard wired external busses such as IEEE-1394 or USB. The computer system can also have a user interface port that communicates with a user interface, and which receives commands entered by a user, and a video output that produces its output via any kind of video output format, e.g., VGA, DVI, HDMI, display port, or any other form. This may include laptop or desktop computers, and may also include portable computers, including cell phones, tablets such as the IPAD™ and Android™ platform tablet, and all other kinds of computers and computing platforms.

A processor may also be implemented as a combination of computing devices, e.g., a combination of a DSP and a microprocessor, a plurality of microprocessors, one or more microprocessors in conjunction with a DSP core, or any other such configuration. These devices may also be used to select values for devices as described herein.

The steps of a method or algorithm described in connection with the embodiments disclosed herein may be embodied directly in hardware, in a software module executed by a processor, using cloud computing, or in combinations. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of tangible storage medium that stores tangible, non-transitory computer based instructions. An exemplary storage medium is coupled to the processor such that the processor can read information from, and write information to, the storage medium. In the alternative, the storage medium may be integral to the processor. The processor and the storage medium may reside in reconfigurable logic of any type.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer.

The memory storage unit(s) can also be rotating magnetic hard disk drives, optical disk drives, or flash memory based storage drives or other such solid state, magnetic, or optical storage devices. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media. The computer readable media can be an article comprising a machine-readable non-transitory tangible medium embodying information indicative of instructions that when performed by one or more machines result in computer implemented operations comprising the actions described throughout this specification.

Operations as described herein can be carried out on or over a web site. The website can be operated on a server computer, or operated locally, e.g., by being downloaded to the client computer, or operated via a server farm. The website can be accessed over a mobile phone or a PDA, or on any other client. The website can use HTML code in any form, e.g., MHTML, or XML, and via any form such as cascading style sheets ("CSS") or other.

The computers described herein may be any kind of computer, either general purpose, or some specific purpose computer such as a workstation. The programs may be written in C, or Java, Brew or any other programming language. The programs may be resident on a storage medium, e.g., magnetic or optical, e.g. the computer hard drive, a removable disk or media such as a memory stick or SD media, or other removable medium. The programs may also be run over a network, for example, with a server or other machine sending signals to the local machine, which allows the local machine to carry out the operations described herein.

Also, the inventors intend that only those claims which use the words "means for" are intended to be interpreted under 35 USC 112, sixth paragraph. Moreover, no limitations from the specification are intended to be read into any claims, unless those limitations are expressly included in the claims.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. An X-ray imaging apparatus, comprising:
an X-ray irradiation unit that is configured to irradiate a subject with X-rays;
an X-ray detection unit that is configured to detect said X-rays transmitted through said subject;
a holding unit that is configured to hold said X-ray irradiation unit and said X-ray detection unit, which face each other;
a table on which said subject is placed;
a drive unit that is configured to rotate the holding unit around a predetermined rotation axis;
a relative position setting unit that is configured to set a relative position of the table with respect to the X-ray irradiation unit and the X-ray detection unit as a set relative position;
a relative position detection unit that is configured to detect a relative position of the table with respect to the X-ray irradiation unit and the X-ray detection unit as a detection relative position;
a comparing unit that is configured to compare the detected relative position with the set relative position;
a control unit that is configured to control the drive unit to start rotating the holding unit so that the X-ray irradiation unit and the X-ray detection unit perform a pendulum motion or a precession motion, when the detected relative position matches the set relative position during the X-ray imaging and relative moving of the table with respect to the X-ray irradiation unit and the X-ray detection unit.

2. The X-ray imaging apparatus, according to claim 1, wherein:
said control unit controls at least one of step of a group of steps consisting of:
a rotating of said holding unit around a predetermined rotation axis, and
a rotating of said holding unit around said predetermined rotation axis based on an operation during said X-ray imaging, while interlocking with a relative position of said table to said X-ray irradiation unit and said X-ray detection unit.

3. The X-ray imaging apparatus, according to claim 2, wherein:
said control unit controls at least one move of:
said holding unit that reciprocate-rotates said X-ray irradiation unit and said X-ray detection unit; and
said holding unit that reciprocate-rotates said X-ray irradiation unit and said X-ray detection unit based on said operation during said X-ray imaging, while interlocking with said relative position of said table to said X-ray irradiation unit and said X-ray detection unit.

4. The X-ray imaging apparatus, according to claim 2, wherein:
said control unit controls at least one movement of said holding unit such that said X-ray irradiation direction of said X-ray irradiation unit and said X-ray detection direction of said X-ray detection unit coincide with a preset direction, and said holding unit such that said X-ray irradiation direction of said X-ray irradiation unit and said X-ray detection direction of said X-ray detection unit coincides with a said preset direction based on said operation during said X-ray imaging, while interlocking with said relative position of said table to said X-ray irradiation unit and said X-ray detection unit.

5. The X-ray imaging apparatus, according to claim 1, wherein:
said control unit controls said X-ray irradiation direction of said X-ray irradiation unit and said X-ray detection direction of said X-ray detection unit by changing a rotation angle of said holding unit.

6. The X-ray imaging apparatus, according to claim 1, wherein:
said X-ray irradiation direction of said X-ray irradiation unit and said X-ray detection direction of said X-ray detection unit are interlockingly controlled, and said relative position of said table to said X-ray irradiation unit and said X-ray detection unit are preset.

7. The X-ray imaging apparatus; according to claim 1, wherein:
said control unit controls a movement of said holding unit that controls said X-ray irradiation direction of said X-ray irradiation unit and said X-ray detection direction of said X-ray detection unit based on that said relative position of said table to said X-ray irradiation unit and said X-ray detection unit reaches a predetermined position.

8. The X-ray imaging apparatus, according to claim 1, wherein:
said X-ray irradiation direction of said X-ray irradiation unit and said X-ray detection direction of said X-ray detection unit are set up in advance in association with said relative position of said table to said X-ray irradiation unit and said X-ray detection unit; and
said control unit controls the move of said holding unit such that said X-ray irradiation direction of said X-ray irradiation unit and said X-ray detection direction of said X-ray detection unit are a preset direction when said relative position of said table to said X-ray irradiation unit and said X-ray detection unit reaches a predetermined intermediate position that is set up in advance.

9. The X-ray imaging apparatus, according to claim 8, wherein:

said X-ray irradiation direction of said X-ray irradiation unit and said X-ray detection direction of said X-ray detection unit are presettable in association with each of a first relative position and a second relative position of said table to said X-ray irradiation unit and said X-ray detection unit; and said control unit controls such that said X-ray irradiation direction of said X-ray irradiation unit and said X-ray detection direction of said X-ray detection unit are a first preset direction when said relative position of said table to said X-ray irradiation unit and said X-ray detection unit reaches a first relative position that is set up in advance, and such that said X-ray irradiation direction of said X-ray irradiation unit and said X-ray detection direction of said X-ray detection unit that are a second preset direction when said relative position of said table to said X-ray irradiation unit and said X-ray detection unit reaches a second relative position set in advance.

10. An X-ray imaging apparatus, comprising:
an X-ray irradiation unit that is configured to irradiate a subject with X-rays;
an X-ray detection unit that is configured to detect said X-rays transmitted through said subject;
a holding unit that is configured to hold said X-ray irradiation unit and said X-ray detection unit, which face each other;
a table on which the subject is placed;
a drive unit that is configured to rotate the holding unit around a predetermined rotation axis;
a relative position setting unit that is configured to set a relative position of the table with respect to the X-ray irradiation unit and the X-ray detection unit as a set relative position;
a relative position detection unit that is configured to detect a relative position of the table with respect to the X-ray irradiation unit and the X-ray detection unit as a detection relative position;
a comparing unit that is configured to compare the detected relative position with the set relative position;
a control unit that is configured to control the drive unit to start rotating the holding unit so that the X-ray irradiation unit and the X-ray detection unit perform a pendulum motion or a precession motion, when the detected relative position matches the set relative position;
wherein the X-ray irradiation direction of the X-ray irradiation unit and the X-ray detection direction of the X-ray detection unit are preset in association with a relative position of the table to the X-ray irradiation unit and the X-ray detection unit during the X-ray imaging and relative moving of the table with respect to the X-ray irradiation unit and the X-ray detection unit.

11. An X-ray photography method by an X-ray imaging apparatus comprising an X-ray irradiation unit that is configured to irradiate a subject with X-rays, an X-ray detection unit that is configured to detect the X-rays transmitted through the subject, a holding unit that is configured to hold the X-ray irradiation unit and the X-ray detection unit, which face each other, a table on which the subject is placed, a driving unit configured to rotate the holding unit around a predetermined rotation axis, and a control unit configured to control the driving unit, comprising;
a step of starting relative movement of the table with respect to the X-ray irradiation unit and the X-ray detection unit;
a step of starting X-ray irradiation from the X-ray irradiation unit;
a step of receiving an operation from a user, during X-ray imaging, while the table is relatively moving with respect to the X-ray irradiation unit and the X-ray detection unit; and
a step of starting rotation of the holding unit by the driving unit by the control unit so that the X-ray irradiation unit and the X-ray detection unit perform a pendulum motion or a precession motion, when the operation from the user is received, during X-ray imaging, while the table is relatively moving with respect to the X-ray irradiation unit and the X-ray detection unit.

12. An X-ray photography method by an X-ray imaging apparatus comprising an X-ray irradiation unit that is configured to irradiate a subject with X-rays, an X-ray detection unit that is configured to detect the X-rays transmitted through the subject, a holding unit that is configured to hold the X-ray irradiation unit and the X-ray detection unit, which face each other, a table on which the subject is placed, a driving unit configured to rotate the holding unit around a predetermined rotation axis, and a control unit configured to control the driving unit, comprising;
a step of starting relative movement of the table with respect to the X-ray irradiation unit and the X-ray detection unit;
a step of starting X-ray irradiation from the X-ray irradiation unit;
a step of receiving an operation from a user, during X-ray imaging, while the table is relatively moving with respect to the X-ray irradiation unit and the X-ray detection unit; and
a step of starting rotation of the holding unit by the driving unit by the control unit so that the X-ray irradiation unit and the X-ray detection unit perform a pendulum motion or a precession motion, when the operation from the user is received during X-ray imaging, while the table is relatively moving with respect to the X-ray irradiation unit and the X-ray detection unit; and
wherein an X-ray irradiation direction of the X-ray irradiation unit and the X-ray detection direction of the X-ray detection unit are preset in association with a relative position of the table to the X-ray irradiation unit and the X-ray detection unit.

* * * * *